United States Patent [19]

Pappalardo

[11] Patent Number: 5,140,862

[45] Date of Patent: Aug. 25, 1992

[54] INJECTION PUMP CALIBRATION DEVICE

[76] Inventor: Joseph T. Pappalardo, 7 Barrymeade Dr., Lexington, Mass. 02173

[21] Appl. No.: 651,310

[22] Filed: Feb. 6, 1991

[51] Int. Cl.⁵ .................................. G01M 19/00
[52] U.S. Cl. ........................... 73/866.4; 73/3; 604/151; 604/154
[58] Field of Search ............ 604/118, 154, 155, 151, 604/152; 73/3, 866.4

[56] References Cited

U.S. PATENT DOCUMENTS

| | | | |
|---|---|---|---|
| 4,324,127 | 4/1982 | Gazzara et al. | 73/3 |
| 4,389,886 | 6/1983 | Korczak | 73/3 |
| 4,537,058 | 8/1985 | Luper | 73/3 |
| 4,627,267 | 12/1986 | Cohrs et al. | 73/3 |
| 4,938,054 | 7/1990 | Dye et al. | 73/3 |

Primary Examiner—Gene Mancene
Assistant Examiner—Michael Lynch
Attorney, Agent, or Firm—Joseph H. Killion

[57] ABSTRACT

An injection pump calibration device insertable in place of an actual syringe in an infusion syringe pump is described. The housing is shaped like a syringe body and configured to detachably mount in place of an actual syringe in an infusion syringe pump. A plunge is affixed to the housing and is moveable between a first position away from the housing and a second position adjacent the housing.

A position detector is adapted to the plunger to measure movement of the plunger between the first position away from the housing and the second position adjacent the housing to calibrate or verify parameters of the infusion syringe pump.

4 Claims, 1 Drawing Sheet

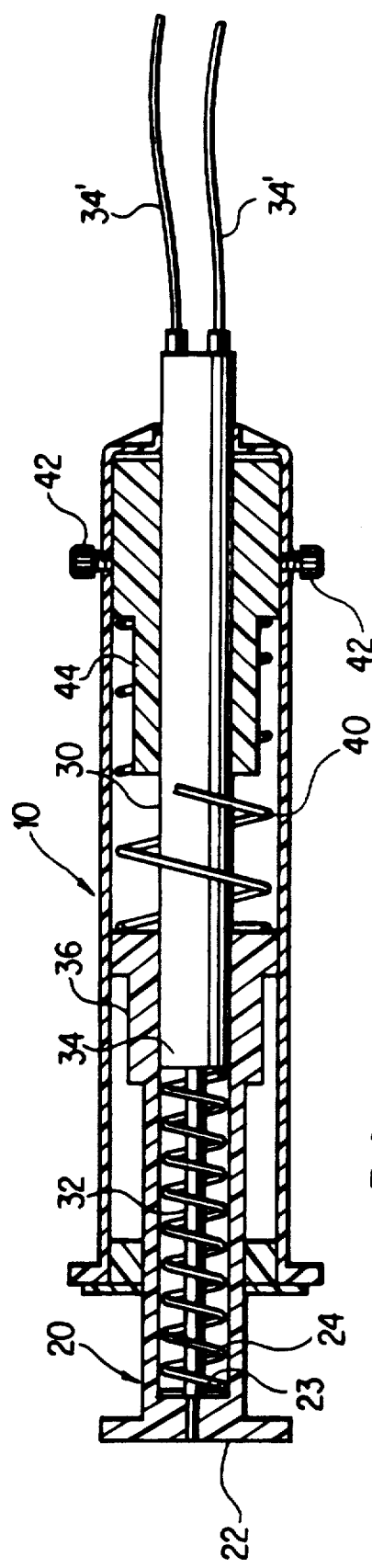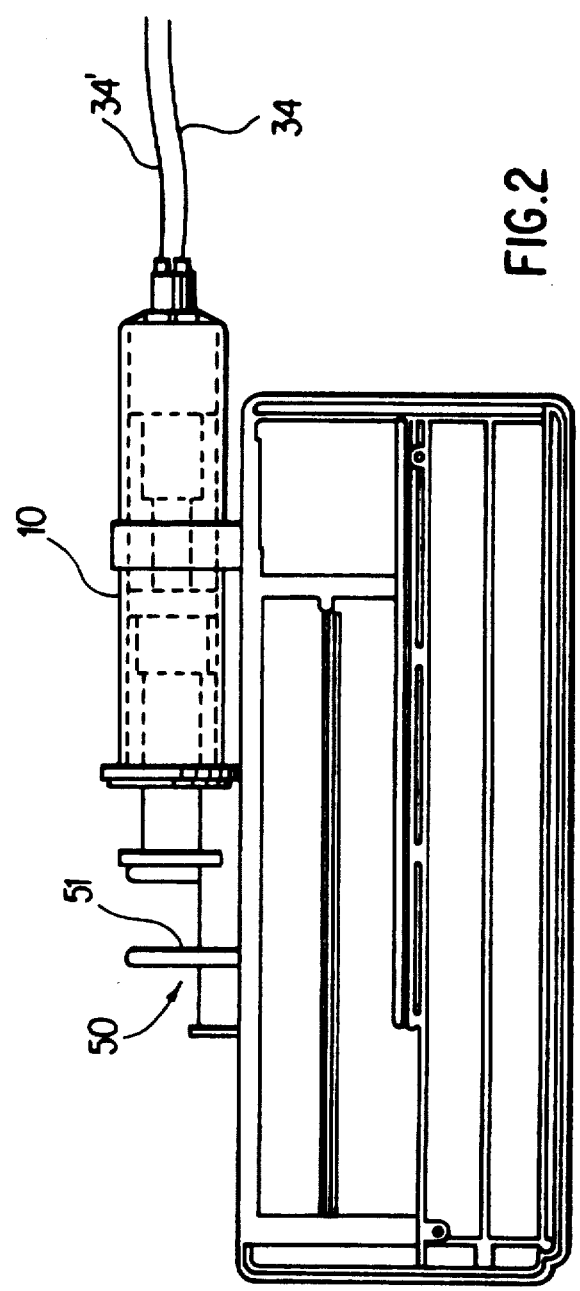

INJECTION PUMP CALIBRATION DEVICE

BACKGROUND OF INVENTION

Syringe infusion pumps, relatively recent inventions, are devices into which a dosage syringe is positioned with the downstream end in an intravenous line connected to a patient and the plunger end against a user programmed drive mechanism. An example of this invention is described in U.S. Pat. No. 4,804,368 (Skakoon) The particular user software program determines the rate of drug injection into the intravenous line.

Syringe infusion pumps have contributed several outstanding advances to the field of medicine. First, medical personnel may be utilized in other important areas at a time when manpower is becoming more of a critical factor.

A second advantage of this infusion pump is that with proper programming, banks of hypodermic syringes containing different dosages and types of drugs being injected into intravenous lines to different patients, may all be controlled from one machine.

The prime technical problem facing Biomedical and Clinical personnel is that infusion pumps must be extremely safe and reliable or the life of the patient is at stake. This level of confidence is mandatory.

Consequently, possible malfunctions have to be addressed in the infusion pump equipment. Possible problems include, but are not limited to, jamming of the plunger within the syringe, possible air bubbles in the line, false starting of the syringe (siphoning), delivery continued beyond the amount of intended dosage and improper delivery rate. Some of these problems have been resolved by the use of alarms and other fail safe mechanisms at certain points in the syringe cycle. See U.S. Pat. No. 4,854,324 (Hirschmam).

However, for patient safety the common practice has been to return the infusion pumps to the manufacturer for verification of the dosages, delivery rates and alarm systems. This procedure is very time-consuming, very expensive, and necessitates a greater number of infusion pumps. Due to the aforementioned facts, many pumps are not verified on a regular basis.

There are several functions of an infusion pump that must be tested to confirm safety and reliability. It is important to note that the rate of delivery is generally in the range of 0.1 mil/hour to 20 mil/hour. Analyzing infusion pumps necessarily includes flow rate determination, culmulative volume determination, individual dosage volume determination, quantity of fluid remaining in the syringe, occlusion pressure, near end of syringe alarms and end of syringe check. Several devices are on the market that provide testing of some, but not all of the above parameters of the infusion pump in situ.

In general, the available testing equipment can only check the rate of fluid flow by pumping a standard fluid (water) through the infusion pumps and then by gravometric or volumetric means determine what the flow rate is against time. Difficulties that exist with these devices are that: the infusion pump analysers must be cleaned, and air bubbles have to be eliminated from the tubings and fittings; maintenance and tubing standardization requirements are difficult to substantiate. The rate of evaporation has to be considered during very slow rates. Also, the delivery rate must be non-pulsing in order to set an accurate reading, and these devices can only measure rates down to 0.5 mils/hour. Finally, the present testing devices are unable to measure occlusion pressure, the amount of liquid left in the syringe, the volume, and can only test one or two infusion pumps simultaneously.

There is then a need for a testing device or method which does not utilize fluids, that tracks the manufacturers method of testing their pumps, that can test the entire range of actual dosage, that can be simply calibrated and connected to the pump, that can quickly test all infusion pumps being used in one software program at the same time, that can test both pulsing and continuous flow pumps, and that is relatively inexpensive to make and use in the field.

SUMMARY OF INVENTION

My invention relates to an infusion pump calibration device and an improved method for verifying critical infusion pumps parameters.

I have discovered an infusion pump analyzing device insertable in place of a syringe in an infusion pump, which comprises, housing means defining a syringe body. Plunger means are affixed to the housing means and moveable between a first position away from said housing means, and a second position substantially adjacent said housing means. A position detecting means is adapted to the plunger means to measure movement of said plunger means between the first position away from the housing means, and a second position substantially adjacent the housing means.

My method for analysing infusion pumps comprises inserting the analyzer into an infusion pump. The pump is then activated and the rate of movement of the plunger is measured by electronic sensor means.

Preferably but optionally my infusion pump analyzing device includes a resisting means in the handle of the plunger of the plunger to simulate back pressure that would cause occlusion or stoppage of the syringe during normal delivery.

The position detecting means will be described in detail in the preferred embodiment. Preferably, and optionally, a transducer is annularly disposed within the housing means, adapted at one end to the end of the plunger, which is moving between the two positions and at the other end to leads which feed the data into the selected display device.

My invention provides numerous advantages over those devices found in the prior art.

Advantages of my invention include that it does not use fluids and consequently there is no rate of evaporation to consider, no cleaning, no leaking, no tubal standardization requirement, no maintenance, no elaborate fittings and no air bubbles in the system.

Other advantages of my invention are that it emmulates the manner in which manufacturers test their pumps, and field data and manufacturer data co-relate.

Also, advantages of my invention are that it can test for rates as low as 0.05 ml/hour with a higher accuracy and precision than what is currently available; that it is easy portable and easy to use with high reliability.

A further and important advantage of my invention is that it can test all infusion pumps being programmed under one software program together and give volume, delivery rates, back pressures and total amount left in syringe.

Further advantages are that it can test both pulsing and continuous flow rates and it can be used quickly and accurately in the field.

BRIEF DESCRIPTION OF THE DRAWINGS

FIG. 1 is a cross-sectional view of the preferred embodiment of the syringe pump.

FIG. 2 is a perspective view of the syringe infusion pump analyzer mounted on an infusion pump.

DETAILED DESCRIPTION OF THE DRAWINGS

Referring now in particular to the accompanying drawings my infusion pump analyzing device is generally indicated in FIG. 1 at 10, and includes a plunger 20, having a finger tab 22 at one end, with an threaded elevated surface 23 inside the plunger 20. Removable spring 24, contacts this elevated surface at one end and at the other end abuts one end of transducer 30, which includes transducer rod 32, extending from the elevated surface 23, to the top of the main transducer body 34.

Compression spring 40, used to simulate normal backpressures, abuts base 26 of the plunger at one end and at the other end abuts transducer housing mount 44. The transducer body 34 extends therethrough and out of the plunger to the end or the transducer which has leads 34. These leads extend to the preferred type of electronic readout. Four set screws 42 extend through the transducer housing contacting the transducer to permit longitudinal adjustments of the transducer.

FIG. 2 shows the infusion pump analyzing device at 10, releasably mounted on an infusion pump 50, to antisiphoning pusher block 51.

Typically in use the infusion pump analyzing device is inserted on the infusion pump. The pusher block and anti-siphoning mechanism of the infusion pump attaches to the finger tab of re infusion pump analyzing device and drives the infusion pump analyzing device at the rate prescribed by the user- program. Data is electrically transmitted to a processing and display device. From these measurement the flow rate can be determined with an accuracy down to approximately 0.05 ml/hour. In addition, the cumulative volume, the volume f individual dosages, the quantity of fluid left in the syringe, instantaneous backpressures and the occlusion pressure as well as whether the system alarms work. In view of the foregoing disclosure, it si seen that the specific advantages are obtained. The disclosure hereof is illustrative and is not intended to limit the scope of the invention. Several modifications, changes and adaptations can be made by those skilled in the art without departing from the scope of the invention. For example, joining the preferred embodiment to different types of transducers (Linear Potentio-meters, Digital Scales, LVit, etc.) will allow the data to be converted into particular information required or specific purposes. Therefore, different means may be substituted by other types of data acquisition units and are anticipated by this invention.

Accordingly, it is the intent of the inventor to include all such modifications which may come within the true scope of the invention which is defined by the appended claims.

What I claim is:

1. A injection pump calibration device insertable in place of an actual syringe in an infusion syringe pump comprising:
    (a) housing means defining a syringe body wherein said housing means is configured to detachably mount in place of said actual syringe in said infusion syringe pump;
    (b) plunger means affixed to said housing means moveable between a first position away from said housing means and a second position substantially adjacent said housing means;
    (c) position detecting means adapting to said plunger means to measure movement of said plunger means between said first position away from said housing means and said second substantially adjacent said housing means to calibrate or verify various parameters of said infusion syringe pump;

2. An injection pump calibration device as in claim 1 wherein said position detecting means is a transducer assembly means.

3. The injection pump calibration device of claim 1 further including:
    a) support means annularly disposed about said transducer assembly means positioned to retain said transducer assembly means in place;
    b) spring means positioned between and end of said housing means on one end thereof and adjacent said plunger means on the other end thereof and arranged to put normal pressure on a down-stroke of said plunger means.

4. An injection pump calibration device insertable in place of an actual syringe in an infusion syringe pump comprising:
    a) housing means defining a syringe body wherein said housing is configured to detachably mount in place of said actual syringe in said infusion syringe pump;
    b) plunger means affixed to said housing moveable between a first position away from said housing means and a second position substantially adjacent said housing means;
    c) transducer assembly means adapting to said plunger means to measure movement of said plunger means between said first position away from said housing means and said second position substantially adjacent said housing to calibrate or verify various parameters of said infusion syringe pump;
    d) support means annularly disposed about said transducer assembly means positioned to retain said transducer assembly means in place;
    e) spring means positioned between an end of said housing means on one end thereof and adjacent said plunger means on the other end thereof and arranged to put normal pressure on a down-stroke of said plunger means.

* * * * *